United States Patent
Feng et al.

(10) Patent No.: US 12,194,072 B2
(45) Date of Patent: Jan. 14, 2025

(54) TRADITIONAL CHINESE MEDICINE COMPOUND FOR PREVENTING AND TREATING AFRICAN SWINE FEVER, AND ITS EFFICIENCY ENHANCEMENT PROCESS AND APPLICATION

(71) Applicant: Henan University of Chinese Medicine, Zhengzhou (CN)

(72) Inventors: Shuying Feng, Luoyang (CN); Sugai Yin, Zhengzhou (CN); Aifang Li, Zhengzhou (CN); Baiyan Wang, Zhengzhou (CN); Dandan Guo, Zhengzhou (CN); Qianqian Wang, Zhengzhou (CN); Yuqiang Zhang, Zhengzhou (CN)

(73) Assignee: Henan University of Chinese Medicine, Zhengzhou (CN)

( * ) Notice: Subject to any disclaimer, the term of this patent is extended or adjusted under 35 U.S.C. 154(b) by 0 days.

(21) Appl. No.: 18/736,592

(22) Filed: Jun. 7, 2024

(65) Prior Publication Data

US 2024/0408161 A1   Dec. 12, 2024

(30) Foreign Application Priority Data

Jun. 9, 2023  (CN) .......................... 202310683404.4

(51) Int. Cl.

| | | |
|---|---|---|
| *A61K 36/00* | (2006.01) | |
| *A61K 36/076* | (2006.01) | |
| *A61K 36/185* | (2006.01) | |
| *A61K 36/24* | (2006.01) | |
| *A61K 36/284* | (2006.01) | |
| *A61K 36/285* | (2006.01) | |
| *A61K 36/344* | (2006.01) | |
| *A61K 36/714* | (2006.01) | |
| *A61K 36/725* | (2006.01) | |
| *A61K 36/8945* | (2006.01) | |
| *A61P 31/20* | (2006.01) | |

(52) U.S. Cl.
CPC .......... *A61K 36/344* (2013.01); *A61K 36/076* (2013.01); *A61K 36/185* (2013.01); *A61K 36/24* (2013.01); *A61K 36/284* (2013.01); *A61K 36/285* (2013.01); *A61K 36/714* (2013.01); *A61K 36/725* (2013.01); *A61K 36/8945* (2013.01); *A61P 31/20* (2018.01); *A61K 2236/19* (2013.01)

(58) Field of Classification Search
CPC ................................................. A61K 2236/19
See application file for complete search history.

(56) References Cited

FOREIGN PATENT DOCUMENTS

CN         105380265 A   *   3/2016

OTHER PUBLICATIONS

CNIPA, Notification of a First Office Action for CN202310683404.4, Mar. 27, 2024.
Henan University of Chinese Medicine (Applicant), Reply to Notification of a First Office Action for CN202310683404.4, w/ replacement claims, Apr. 16, 2024.
Henan University of Chinese Medicine (Applicant), Supplemental Reply to Notification of a First Office Action for CN202310683404.4, w/ (allowed) replacement claims, Apr. 19, 2024.
CNIPA, Notification to grant patent right for invention in CN202310683404.4, Apr. 24, 2024.

* cited by examiner

*Primary Examiner* — Qiuwen Mi
(74) *Attorney, Agent, or Firm* — Hemisphere Law, PLLC; Zhigang Ma

(57) ABSTRACT

A traditional Chinese medicine compound for preventing and treating African swine fever, its efficiency enhancement process, and application are provided, which relate to the field of fermentation technologies of traditional Chinese medicine by probiotics. A formula with the most apparent preventive and therapeutic effect on ASFV is obtained by comparing various traditional Chinese medicine prescriptions and self-drafted formulas, and the formula is made from *Codonopsis pilosula, Atractylodes macrocephala, Wolfiporia cocos, Auckiandialappa Lappa* Decne., *Terminalia chebula, Aconitum carmichaeli, Myristica fragrans, Cynanchum otophyllum, Dioscorea polystachya* and *Ziziphus jujuba*. Based on the formula, fermentation treatment of multi probiotics is performed, *Bacillus subtilis, Saccharomyces cerevisiae, Bifidobacterium* and *Lactobacillus acidophilus* are inoculated for fermenting, and a liquid fermented mixture is mixed to obtain fermentation preparation. The traditional Chinese medicine compound has a definite therapeutic effect, reasonable compatibility, a wide range of materials, and a low price, which makes it easy to promote and apply.

4 Claims, 2 Drawing Sheets

TRADITIONAL CHINESE MEDICINE COMPOUND FOR PREVENTING AND TREATING AFRICAN SWINE FEVER, AND ITS EFFICIENCY ENHANCEMENT PROCESS AND APPLICATION

CROSS-REFERENCE TO RELATED APPLICATION

This application claims priority to Chinese Patent Application No. 202310683404.4, filed on Jun. 9, 2023, which is herein incorporated by reference in its entirety.

TECHNICAL FIELD

The disclosure relates to the field of fermentation technologies of traditional Chinese medicine by probiotics, and more particularly to a traditional Chinese medicine compound for preventing and treating African swine fever, an efficiency enhancement process and an application thereof.

BACKGROUND

African swine fever (ASF) is an acute, hemorrhagic and virulent infectious disease caused by the African swine fever virus (ASFV) infecting domestic pigs and various wild boars. It is classified as a legally reported animal disease by the World Organization for Animal Health (WOAH) and as a Class I infectious disease by China. The ASF is characterized by high fever, skin cyanosis, and severe bleeding from lymph nodes and internal organs, and it has a short onset process, fast onset, strong infectivity, and a high acute mortality rate. Most animals infected with the ASF will die during the treatment process. After the discovery of the first ASF case in Shenyang, Liaoning, China, in August 2018, a spatial circulation pattern of "west to east pig transport, north to south pig transport" caused the ASF situation to quickly spread to many parts of the country, posing a massive threat to pig breeding industry in China. The ASF has directly or indirectly caused billions of yuan in economic losses in China, with a large number of domestic pigs and diseased pigs being hunted and killed, posing a massive threat to the pig breeding industry in China and becoming a challenge for global livestock production.

At present, the primary method for preventing and treating ASF is to use culling, and there are currently no effective drugs or vaccines in the world to prevent and control the disease. Using traditional Chinese medicine against viruses has become a hot topic in modern medical research, and many traditional Chinese medicines have shown significant antiviral effects. In the absence of effective products in modern medicine to prevent and control ASF, a combination of traditional Chinese medicine and modern preparation technology has apparent advantages in preventing and treating ASF.

SUMMARY

Aiming at the above problems, the disclosure's primary purpose is to provide a traditional Chinese medicine compound for preventing and treating ASF.

Another purpose of the disclosure is to provide an efficiency enhancement process of the above traditional Chinese medicine compound.

Still, another purpose of the disclosure is to provide an application of the above traditional Chinese medicine compound, and the application includes: preparing a drug for preventing and treating ASF by using the traditional Chinese medicine compound.

The disclosure provides a traditional Chinese medicine compound for preventing and treating ASF, and the compound's effect is significantly improved through a probiotic fermentation process.

In order to achieve the above purposes, specific solutions used by the disclosure are as follows.

In the first aspect, a traditional Chinese medicine compound for preventing and treating ASF is provided, and the traditional Chinese medicine compound is made from the following raw materials in parts by weight:

10-20 parts of *Codonopsis pilosula*, 10-20 parts of *Atractylodes macrocephala*, 10-20 parts of *Wolfiporia cocos*, 3-9 parts of *Auckiandialappa Lappa* Decne., 5-15 parts of *Terminalia chebula*, 3-9 parts of *Aconitum carmichaeli*, 5-15 parts of *Myristica fragrans*, 9-15 parts of *Cynanchum otophyllum*, 20-40 parts of *Dioscorea polystachya* and 2-5 parts of *Ziziphus jujuba*.

The Chinese herbal medicine components selected by the disclosure have the following effects.

The traditional Chinese medicine compound in the disclosure plays to the overall concept and dialectical treatment theory of traditional Chinese medicine, which can effectively prevent and treat ASF disease. The ASF is considered a plague in traditional Chinese medicine, and treatment principles adopted from the perspective of traditional Chinese medicine are "strengthening vital qi, eliminating pathogenic qi, and avoiding toxic qi". "When a person contracts plague caused by an epidemic miasma of heaven and Earth, pathogenic factors enter the body through mouth and nose; they reside neither within viscera nor along meridians but remain within a position of deep muscles of the body. The position is neither on the body surface nor deep into internal organs but between the body surface and the internal organs near the stomach. The position is a transitional area between exterior and interior; thus, it is known as the half-exterior and half-interior." According to a development of the disease, when the person experiences rapid high fever, decreased appetite, weakness, shortness of breath, coughing, vomiting, and diarrhoea, it is necessary to use drugs that clear heat and resolve toxins, as well as cool blood and resolve stasis, so that heat toxins can be quickly eliminated from lower-Jiao (including the small intestine, large intestine, kidney and urinary bladder). At the same time, protecting the primordial qi of the spleen and the kidney is necessary. A leading source of external qi in human and animal bodies is spleen-stomach qi; the spleen-stomach belongs to the Earth and affects the functions of the viscera of humans and animals. Symptoms of decreased appetite, weakness, vomiting, and diarrhoea of the ASF are performances of hypofunction of the spleen and the stomach. The traditional Chinese medicine compound is modified Shenling Baizhu powder (i.e., *Codonopsis pilosula*, *Wolfiporia cocos*, the *Atractylodes macrocephala* and the like), mainly used to prevent and treat ASF.

The *Codonopsis pilosula* has a sweet taste and a mild nature and is beneficial for the spleen and lungs. Moreover, the *Codonopsis pilosula* has effects of tonifying middle-Jiao (including the spleen, stomach, liver and gallbladder) and qi, invigorating the spleen and tonifying the lungs. The *Codonopsis pilosula* is used for hypofunction of the spleen and stomach, weakness, poor appetite, chronic diarrhoea and rectal prolapse. The *Atractylodes macrocephala* has a bitter taste and a warm nature and has the effects of invigorating the spleen and tonifying qi, eliminating dampness and promoting diuresis. Moreover, *Atractylodes macrocephala* treats hypofunction in the spleen, poor appetite, abdominal distension, and diarrhoea. The *Wolfiporia cocos* have a sweet taste and a mild nature and are beneficial for the heart, lungs and spleen. Moreover, *Wolfiporia cocos* have the effects of promoting diuresis and invigorating the spleen and are used for diarrhoea and dyspepsia. The *Auckiandialappa Lappa* Decne. has the effects of regulating qi to harmonize the stomach and invigorate the spleen to aid digestion. The *Myristica fragrans* can treat deficiency diarrhoea, cold dysentery, abdominal cold pain and vomiting. The *Cynanchum otophyllum* has the effects of nourishing yin and promoting the production of body fluid, as well as relieving spasms and pain. The *Dioscorea polystachya* has effects of invigorating the spleen and tonifying the lungs, as well as reinforcing the kidney to produce essence, and is used for hypofunction of the spleen and the stomach, and diarrhoea. Compatibility of the *Wolfiporia cocos*, the *Codonopsis pilosula*, the *Atractylodes macrocephala* and the *Dioscorea polystachya* medicines can reinforce the qi of the lungs and the spleen. Compatibility of the *Aconitum carmichaeli*, the *Auckiandialappa Lappa* Decne., the *Terminalia chebula* and the *Wolfiporia cocos* medicines is mainly used for deficiency and weakness of the internal organs and qi. A combination of the above medicines involves invigorating the spleen and tonifying qi, resolving dampness and stopping diarrhoea, and warming and strengthening the spleen and the kidney. The traditional Chinese medicine compound is suitable for hyperfunctioning the spleen and stomach, and symptoms of rapid diarrhoea or chronic diarrhoea of the ASF cause the failure of viscera-qi.

In a second aspect, an efficiency enhancement process of the above traditional Chinese medicine compound by probiotic is provided, and the probiotic efficiency enhancement process includes:

step 1, mixing, according to the parts by weight, the *Codonopsis pilosula*, the *Atractylodes macrocephala*, the *Wolfiporia cocos*, the *Auckiandialappa Lappa* Decne., the *Terminalia chebula*, the *Aconitum carmichaeli*, the *Myristica fragrans*, the *Cynanchum otophyllum*, the *Dioscorea polystachya* and the *Ziziphus jujuba* to obtain a first mixture, performing nanoparticle crushing on the first mixture to obtain mixed powder;

step 2, mixing the mixed powder obtained in step 1 with a fermentation medium, placing the fermentation medium mixed with the mixed powder into a primary fermenter, inoculating *Bacillus subtilis* and *Saccharomyces cerevisiae* in the primary fermenter to obtain a second mixture, stirring the second mixture continuously at 30-38 Celsius degrees (° C.) for 12-48 hours (h); where air is introduced into the primary fermenter containing the second mixture during the stirring for aerobic fermentation to obtain an intermediate product;

step 3 adding the intermediate product into 30% volume of the fermentation medium for stirring evenly, placing the fermentation medium added with the intermediate product into a secondary fermenter, adding anaerobic fermentation microorganisms *Lactobacillus acidophilus* and *Bifidobacterium* into the secondary fermenter to obtain a third mixture, placing the secondary fermenter containing the third mixture into a fermentation bag with a one-way exhaust valve for anaerobic fermentation at 28-42° C. for 1-5 days (d) to obtain a liquid finish product (also referred to a fermented mixture); and step 4, obtaining a traditional Chinese medicine compound fermented preparation, wherein the obtaining a traditional Chinese medicine compound fermented preparation includes one step selected from the group consisting of:

directly aseptically filling the fermented mixture to obtain a fluid dosage form;

filtering the fermented mixture to obtain a filtered mixture, aseptically filling the filtered mixture to obtain a liquid dosage form; and performing a low-temperature spray drying treatment on the fermented mixture to obtain a powder dosage form.

In steps 2 and 3, an inoculation ratio of the *Bacillus subtilis, Saccharomyces cerevisiae, Bifidobacterium*, and *Lactobacillus acidophilus* is 2:1:1:1. A fermentation condition in the primary fermenter and the secondary fermenter is as follows: 0.01-0.2 kilopascals (kPa) of pressure, 15-35 revolutions per minute (r/min) of stirring speed, and 6.1-7.2 of power of hydrogen (pH) value. An addition ratio of the mixed powder and the fermentation medium is 10-25 g: 1 liter (L). The *Bacillus subtilis* can stimulate the growth and development of the immune organs of the animal, activate T and B lymphocytes, improve levels of immunoglobulins and antibodies, enhance cellular and humoral immune functions, and thereby improve the immunity and antiviral ability of the animal. Meanwhile, *Bacillus subtilis* can synthesize B1, B2, B6, nicotinic acid and other B vitamins to supplement the vitamins in animals, which is beneficial to the growth of pigs. The *Saccharomyces cerevisiae* can convert glucose in traditional Chinese medicine into ethanol so that traditional Chinese medicine substances can produce wine aroma to promote the appetite of the pigs, and the *Saccharomyces cerevisiae* have the function of antisepsis. The *Lactobacillus acidophilus* can adjust a balance of intestinal flora and inhibit the proliferation of undesirable intestinal microorganisms. A leaven mixed with the *Bifidobacterium* can produce lactic acid and acetic acid after fermentation in the gut. This can improve the utilization rate of calcium, phosphorus and iron and promote absorption of iron and vitamins. Consuming food containing the two types of live bacteria can quickly restore an average balance of the intestinal flora, inhibit the proliferation of spoilage bacteria, and especially have good nutritional and health benefits for piglets with gastrointestinal dysfunction.

On the one hand, the traditional Chinese medicine produced through probiotic fermentation is more suitable for pigs to eat. The raw materials of traditional Chinese medicine are decomposed more thoroughly, and some substrates, such as ketones and esters, are further precipitated, which facilitates digestion and absorption of the pigs to improve the utilization rate of the medicinal materials. Traditional Chinese medicine is particularly suitable for piglets whose intestines and stomach are not entirely sound, without causing resistance and gastrointestinal discomfort in the piglets. On the other hand, consuming the fermented preparation containing live probiotics can improve the imbalance of the intestinal flora. In summary, the fermented traditional Chinese medicine preparation has significantly improved taste and efficacy compared to a non-fermented preparation.

In steps 2 and 3, a formula of the fermentation medium in the primary fermenter and the secondary fermenter includes 10 grams (g) of refined peptone, 40 g of glucose, 5 g of sodium acetate, 2 g of ammonium citrate, 0.1 g of polysorbate 80 (also referred to as TWEEN® 80), 0.58 g of magnesium sulfate, 0.28 g of manganese sulfate and 1000 milliliters (mL) of distilled water; a pH of the fermentation medium is adjusted to 6-7 by using a 10% sodium hydroxide solution, and then the fermentation medium is autoclaved at 121° C. for 20 minutes (min).

In a third aspect, the above traditional Chinese medicine compound fermented preparation is applied to prevent and treat ASF, and the application includes steps of prevention and treatment.

The prevention includes the following steps. The traditional Chinese medicine compound fermented preparation is made from the following raw materials in parts by weight: 10-20 parts of *Codonopsis pilosula*, 10-20 parts of *Atractylodes macrocephala*, 10-20 parts of *Wolfiporia cocos*, 3-9 parts of *Auckiandialappa Lappa* Decne., 5-15 parts of *Terminalia chebula*, 3-9 parts of *Aconitum carmichaeli*, 5-15 parts of *Myristica fragrans*, 9-15 parts of *Cynanchum otophyllum*, 20-40 parts of *Dioscorea polystachya* and 2-5 parts of *Ziziphus jujuba*. The raw materials are mixed and crushed to obtain mixed powder. The mixed powder is fermented with the *Bacillus subtilis*, the *Saccharomyces cerevisiae*, the *Bifidobacterium* and the *Lactobacillus acidophilus* in stages to obtain a fermented mixture, a ratio of the *Bacillus subtilis*:the *Saccharomyces cerevisiae*:the *Bifidobacterium*: the *Lactobacillus acidophilus* is 2:1:1:1, and contents of the *Bacillus subtilis*, the *Saccharomyces cerevisiae*, the *Bifidobacterium* and the *Lactobacillus acidophilus* are greater than or equal to $1.0 \times 10^7$ colony forming units per liter (CFU/L). After fermenting, the fermented mixture is frozen and dried at low temperatures to obtain the traditional Chinese medicine compound fermented preparation. The traditional Chinese medicine compound fermented preparation is mixed with pig feed for feeding the pig according to the weights of a frozen-dried product of the traditional Chinese medicine compound fermented preparation once a day. The pig is fed for 7 consecutive days during the ASF, and the feeding ratio of the weights of the frozen-dried product of the traditional Chinese medicine compound fermented preparation and weights of the pig is 0.1 g: 1 kilogram (kg).

The treatment includes the following steps. The traditional Chinese medicine compound fermented preparation is made from the following raw materials in parts by weight: 10-20 parts of *Codonopsis pilosula*, 10-20 parts of *Atractylodes macrocephala*, 10-20 parts of *Wolfiporia cocos*, 3-9 parts of *Auckiandialappa Lappa* Decne., 5-15 parts of *Terminalia chebula*, 3-9 parts of *Aconitum carmichaeli*, 5-15 parts of *Myristica fragrans*, 9-15 parts of *Cynanchum otophyllum*, 20-40 parts of *Dioscorea polystachya* and 2-5 parts of *Ziziphus jujuba*. The raw materials are mixed and crushed to obtain mixed powder. The mixed powder is fermented with the *Bacillus subtilis*, the *Saccharomyces cerevisiae*, the *Bifidobacterium* and the *Lactobacillus acidophilus* in stages to obtain a fermented mixture, a ratio of the *Bacillus subtilis*:the *Saccharomyces cerevisiae*:the *Bifidobacterium*: the *Lactobacillus acidophilus* is 2:1:1:1, and contents of the *Bacillus subtilis*, the *Saccharomyces cerevisiae*, the *Bifidobacterium* and the *Lactobacillus acidophilus* are more significant than and equal to $1.0 \times 10^7$ CFU/L. After fermenting, the fermented mixture is frozen and dried at low temperatures to obtain the traditional Chinese medicine compound fermented preparation. The traditional Chinese medicine compound fermented preparation is mixed with the pig feed, feeding the pig according to the weights of the frozen-dried product of the traditional Chinese medicine compound fermented preparation once a day. The feeding ratio of the weights of the frozen-dried product of the traditional Chinese medicine compound fermented preparation and the pig weights are 0.2 g: 1 kg. The traditional Chinese medicine compound fermented preparation is mixed with the pig feed for feeding the pig for 7 consecutive days from the onset of symptoms and consolidated for 5 days after controlling the symptoms.

The administration is through the gastrointestinal tract. A dosage form of the traditional Chinese medicine compound fermented preparation can be selected from the group consisting of a liquid dosage form after fermenting, a powder dosage form prepared by low-temperature spray drying the fermented mixture, a fluid dosage form, a granule dosage form, and a pill dosage form.

The disclosure has the following advantages compared to the related art.

(1) The disclosure has conducted a comparative analysis of the antiviral effects of various traditional Chinese medicine formulas (3 classic formulas, 3 self-formulated formulas, and 3 traditional Chinese medicine monomers), and the results show that the disclosure's traditional Chinese medicine compound has the best antiviral effect.

(2) The disclosure has conducted a comparative analysis of the fermentation effects of different combinations of *Bacillus subtilis*, *Saccharomyces cerevisiae*, *Bifidobacterium* and *Lactobacillus acidophilus*. The results show that the different combinations of the four bacteria are optimal when the ratio of the four bacteria is 2:1:1:1, to successfully establish the efficiency enhancement process of the traditional Chinese medicine compound.

(3) To improve the effect of traditional Chinese medicine compounds, the disclosure performs ultra-fine crushing on them. It directly utilizes all drugs without the need for purification, which is different from a water extraction method of effective ingredients in traditional Chinese medicine.

(4) Macromolecular substances in traditional Chinese medicine can be transformed into small molecular components that the gut of the body can directly absorb through microorganisms after the traditional Chinese medicine is fermented by the probiotics in stages, which can increase the further precipitation of practical components of the traditional Chinese medicine, such as ketones, esters and other substances, improve the drug absorption capacity, help improve a biotransformation effect and the utilization rate of medicinal materials, and enhance the antiviral effect. Moreover, the traditional Chinese medicine compound fermented preparation is more suitable for pigs to eat, especially for the piglets whose intestines and stomach are not entirely sound, without causing resistance and gastrointestinal discomfort in the piglets.

(5) The raw materials of the traditional Chinese medicine compound fermented preparation of the disclosure are widely available for easy access and low price. The preparation method is simple and easy to operate. Traditional Chinese medicine is fermented, which combines the advantages of traditional Chinese medicine and probiotics. The traditional Chinese medicine compound fermented preparation of the disclosure has a short production cycle, low cost, and a convenient and controllable processing process, which is suitable for the mass production requirements of pig farmers.

DETAILED DESCRIPTION OF EMBODIMENTS

Figure 1:
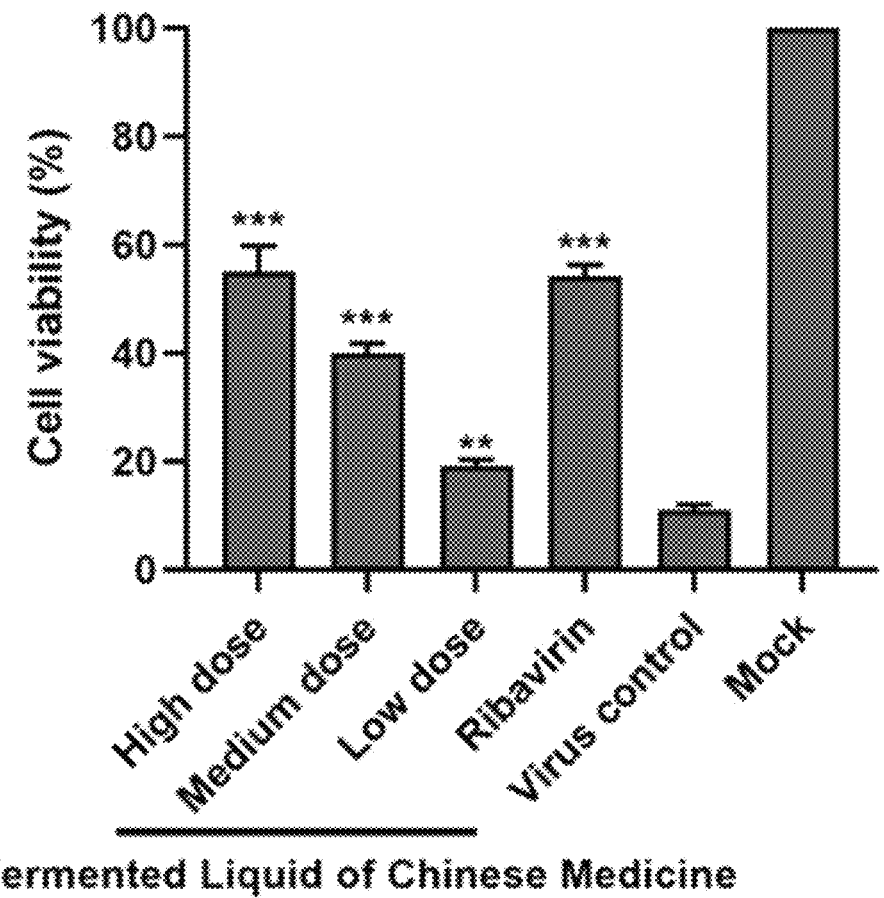
FIG. 1 illustrates a schematic diagram of a tissue culture infectious dose 50 ($TCID_{50}$) test result of a traditional Chinese medicine compound against ASFV according to an embodiment of the disclosure.

Technical solutions in embodiments of the disclosure are clearly and completely described in conjunction with the embodiments of the disclosure below.

The embodiments of the disclosure are described in detail in conjunction with actual situations.

Embodiment 1 Identification of the Anti-ASFV Effect of a Traditional Chinese Medicine Compound The traditional Chinese medicine compound of the disclosure is made from the following raw materials in parts by weight: 20 g of *Codonopsis pilosula*, 20 g of *Atractylodes macrocephala*, 20 g of *Wolfiporia cocos*, 9 g of *Auckiandialappa Lappa* Decne., 15 g of *Terminalia chebula*, 9 g of *Aconitum carmichaeli*, 15 g of *Myristica fragrans*, 15 g of *Cynanchum otophyllum*, 40 g of *Dioscorea polystachya* and 5 g of *Ziziphus jujuba*. The raw materials are mixed and crushed to obtain mixed powder. The mixed powder is fermented with *Bacillus subtilis*, *Saccharomyces cerevisiae*, *Bifidobacterium* and *Lactobacillus acidophilus* in stages to obtain the traditional Chinese medicine compound, and contents of the *Bacillus subtilis*, the *Saccharomyces cerevisiae*, the *Bifidobacterium* and the *Lactobacillus acidophilus* are greater than or equal to $1.0 \times 10^7$ CFU/L. The virus strain used in the experiment is the ASFV gene type II strain (ASFV CN/SC/2019), which is an isolated strain from the African swine fever regional laboratory of the Lanzhou Veterinary Research Institute of the Chinese Academy of Agricultural Sciences, a virus potency is $5 \times 10^7$ TCID$_{50}$/mL, a multiplicity of infection (MOI) of the ASFV CN/SC/2019 virus strain is 0.1.

1. Kidney cells of African *Chlorocebus sabaeus* (Vero cells) are cultivated as follows: 5 mL of serum (purchased from Biological industries) and 500 microliters (L) of double antibody (i.e., penicillin and streptomycin) are added into each 45 mL of a Dulbecco's modified Eagle's medium (DMEM), and the DMEM added with the serum and the double antibody is stored in a refrigerator at 4° C. after mixing evenly.

2. The Vero cells are divided into five groups that are a treatment group with a low dose of traditional Chinese medicine compound, a treatment group with a medium dose of traditional Chinese medicine compound (i.e., fermented liquid of Chinese medicine), a treatment group with a high dose of traditional Chinese medicine compound, a ribavirin group and a virus alone infection group (i.e., virus control), and each group has three replicates. In all groups, serum-free but 0.1% pancreatin-containing culture medium is used. The Vero cells with good growth status are inoculated at a 12-well plate, the serum-free but 0.1% pancreatin-containing culture medium is discarded when a cell confluence degree reaches 90%, and then the Vero cells are washed with phosphate-buffered saline (PBS) twice. The Vero cells are infected with the ASFV (MOI=0.1) in the treatment groups (i.e., the treatment group with the low dose of traditional Chinese medicine compound, the treatment group with the medium dose of traditional Chinese medicine compound, the treatment group with the high dose of traditional Chinese medicine compound) and the virus alone infection group, after 1 h of virus adsorption, the Vero cells are washed with PBS twice. The treatment groups are added with 1.5 mL of the traditional Chinese medicine compound (concentrations are 250 micrograms per milliliter abbreviated as g/mL, 500 μg/mL and 1000 g/mL, respectively) and continuously cultivated for 24 h. Pathological conditions of the Vero cells are observed and photographed under a microscope.

3. As samples, the 12-well plate with the Vero cells from step 2 is collected and placed at −80° C. for three freeze-thaw cycles. DMEM without serum is used to dilute the samples 10 times continuously to obtain samples with 10 dilutions; each dilution is repeated in 8 wells and inoculated until they are complete for culture, and the cell plates inoculated with the samples are cultured under 37° C. and 5% carbon dioxide ($CO_2$) conditions. The pathological condition in each cell culture well is observed and recorded daily for 5 consecutive days. TCID$_{50}$ of the virus solution is calculated according to a Reed-Muench formula. TCID$_{50}$=logarithm of reciprocal of high critical dilution for 50% infection+distance ratio×logarithm of dilution coefficient.

As shown in FIG. 1, the result shows that compared to the virus alone infection group, a virus titer (P<0.05) in the treatment group with low dose traditional Chinese medicine compound is significantly decreased, virus titers (P<0.01) in the treatment group with medium dose traditional Chinese medicine compound and the treatment group with high dose traditional Chinese medicine compound are extremely significantly decreased. Therefore, the traditional Chinese medicine compound's antiviral effect is dependent

Embodiment 2 Influence of Tetra-Strain Fermentation Product on the Activity of the ASFV The tetra-strain fermentation product (i.e., traditional Chinese medicine compound fermented preparation) of the disclosure is made from the following raw materials in parts by weight: 10 g of *Codonopsis pilosula*, 10 g of *Atractylodes macrocephala*, 10 g of *Wolfiporia cocos*, 3 g of *Auckiandialappa Lappa* Decne., 5 g of *Terminalia chebula*, 3 g of *Aconitum carmichaeli*, 5 g of *Myristica fragrans*, 9 g of *Cynanchum otophyllum*, 20 g of *Dioscorea polystachya* and 2 g of *Ziziphus jujuba*. The raw materials are mixed and crushed to obtain mixed powder. The mixed powder is placed into a primary fermenter, and the *Bacillus subtilis* and the *Saccharomyces cerevisiae* are inoculated in the primary fermenter to obtain a mixture; the mixture is stirred continuously at 37° C. for 24 h. During stirring, air is introduced into the primary fermenter containing the mixture for aerobic fermentation to obtain an intermediate product. Half of the intermediate product is placed into a secondary fermenter, and anaerobic fermentation microorganisms *Lactobacillus acidophilus* and *Bifidobacterium* are added into the secondary fermenter with half of the intermediate product. The secondary fermenter is placed into a fermentation bag with a one-way exhaust valve for anaerobic fermentation at 33° C. for 3 d to obtain a fermented mixture. Contents of the *Bacillus subtilis*, the *Saccharomyces cerevisiae*, the *Bifidobacterium* and the *Lactobacillus acidophilus* are greater than or equal to $1.0 \times 10^7$ CFU/L. Fermentation effects of different combinations of the *Bacillus subtilis*, *Saccharomyces cerevisiae*, *Bifidobacterium* and *Lactobacillus acidophilus* are compared, and ratios of the different combinations are 1:1:1:1, 1:2:2:1, 1:1:2:2 and 2:1:1:1, respectively. The fermented mixture is directly aseptically filled in a fluid dosage form. A low-temperature spray drying treatment is performed on the fermented mixture to obtain the traditional Chinese medicine preparation fermented with probiotics. The virus strain used in the experiment is the ASFV gene type II strain (ASFV CN/SC/2019), which is an isolated strain from the African swine fever regional laboratory of the Lanzhou Veterinary Research Institute of the Chinese Academy of Agricultural Sciences, a virus potency is $5 \times 10^7$ TCID$_{50}$/mL, MOI of the ASFV CN/SC/2019 virus strain is 0.1.

1. Kidney cells of African *Chlorocebus sabaeus* (Vero cells) are cultivated as follows: 5 mL of serum (purchased from Biological industries) and 500 µL of double antibody (i.e., penicillin and streptomycin) are added into each 45 mL of DMEM, and the DMEM added with the serum and the double antibody is stored in a refrigerator at 4° C. after mixing evenly.

2. The Vero cells are divided into five groups that are fermentation groups with the different combinations of the four bacteria with ratios of 1:1:1:1, 1:2:2:1, 1:1:2:2 and 2:1:1:1, and a pure traditional Chinese medicine compound group, and each group has three replicates. In all groups, serum-free but 0.1% pancreatin-containing culture medium is used. The Vero cells with good growth status are inoculated at a 12-well plate, the serum-free but 0.1% pancreatin-containing culture medium is discarded when a cell confluence degree reaches 90%, and then the Vero cells are washed with PBS twice. The Vero cells are infected with the ASFV (MOI=0.1) in the fermentation groups and the pure traditional Chinese medicine compound group; after 1 h of virus adsorption, the Vero cells are washed with PBS twice. The fermentation and pure traditional Chinese medicine compound groups are added with 1.5 mL of the traditional Chinese medicine compound (concentrations are 500 µg/mL). They are continuously cultivated for 24 hours to collect samples.

3. DMEM without serum is used to dilute the samples 10 times continuously to obtain samples with 10 dilutions; each dilution is repeated in 8 wells and inoculated until they are complete for culture, and the cell plates inoculated with the samples are cultured under 37° C. and 5% CO$_2$ conditions. The pathological condition in each cell culture well is observed and recorded daily for 5 consecutive days. TCID$_{50}$ of the virus solution is calculated according to the Reed-Muench formula. TCID$_{50}$=logarithm of reciprocal of high critical dilution for 50% infection+distance ratio×logarithm of dilution coefficient.

Figure 2:
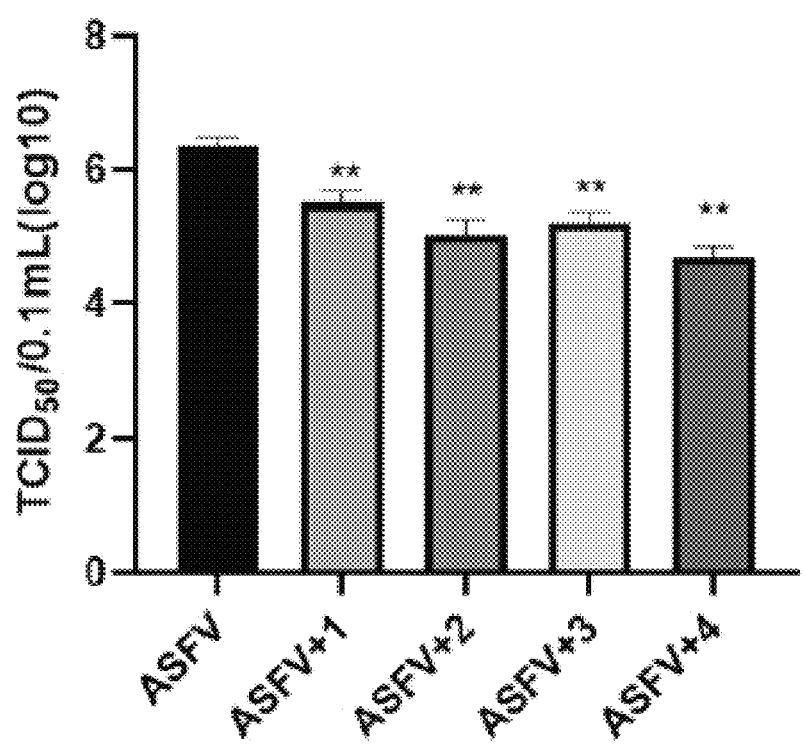
FIG. 2 illustrates a schematic diagram of the effect of tetra-strain fermentation products on the activity of the ASFV according to an embodiment of the disclosure.

As shown in FIG. 2, the fermentation effects of the different combinations of *Bacillus subtilis*, *Saccharomyces cerevisiae*, *Bifidobacterium* and *Lactobacillus acidophilus* are compared, the ratios of the different combinations are 1:1:1:1, 1:2:2:1, 1:1:2:2 and 2:1:1:1, respectively, and the different combinations are labelled as ASFV+1, ASFV+2, ASFV+3 and ASFV+4. It can be seen from the result that the antiviral effects of the fermentation groups are more significant than the pure traditional Chinese medicine compound group, and the ASFV+4 group has the optimal antiviral effect. That is, when the ratio of the combination is 2:1:1:1, the virus titer is the lowest, and the antiviral effect is optimal.

Embodiment 3 Actual Prevention Effect of the Tetra-Strain Fermentation Product on the ASFV A traditional Chinese medicine compound fermented preparation for treating ASFV is provided. The traditional Chinese medicine compound fermented preparation is made from the following raw materials in parts by weight: 15 g of *Codonopsis pilosula*, 15 g of *Atractylodes macrocephala*, 15 g of *Wolfiporia cocos*, 6 g of *Auckiandialappa Lappa* Decne., 10 g of *Terminalia chebula*, 6 g of *Aconitum carmichaeli*, 10 g of *Myristica fragrans*, 12 g of *Cynanchum otophyllum*, 30 g of *Dioscorea polystachya* and 3 g of *Ziziphus jujuba*. The raw materials are mixed and crushed to obtain mixed powder. The mixed powder is placed into a primary fermenter, and the *Bacillus subtilis* and the *Saccharomyces cerevisiae* are inoculated in the primary fermenter to obtain a mixture; the mixture is stirred continuously at 38° C. for 48 h. During stirring, air is introduced into the primary fermenter containing the mixture for aerobic fermentation to obtain an intermediate product. Half of the intermediate product is placed into a secondary fermenter, anaerobic fermentation microorganisms *Lactobacillus acidophilus* and *Bifidobacterium* are added into the secondary fermenter with half of the intermediate product, and the secondary fermenter is placed into a fermentation bag with one-way exhaust valve for anaerobic fermentation at 37° C. for 2 d to obtain a fermented mixture. Contents of the *Bacillus subtilis*, the *Saccharomyces cerevisiae*, the *Bifidobacterium* and the *Lactobacillus acidophilus* are greater than or equal to $1.0 \times 10^7$ CFU/L. The fermented mixture is directly aseptically filled in a fluid dosage form. A low-temperature spray drying treatment is performed on the fermented mixture to obtain the traditional Chinese medicine preparation fermented with probiotics.

A pig farm in Nanyang, Henan, has over 3000 sows. From April to June 2021, an ASF epidemic broke out in the surrounding pig farms of this pig farm, which once caused more than 90% of the pig farms to close down and clear the fields. The site selection of the pig farm has a reasonable layout, scientific pig farm management, and strict disinfection and prevention measures for people, cars and animals entering the farm. The pig farm controls biological safety well and focuses on protecting susceptible pig populations. The traditional Chinese medicine preparations were mixed into pig feed for feeding the pig based on the weight of freeze-dried traditional Chinese medicine compound once a day. The feeding ratio of the frozen-dried traditional Chinese medicine compound and the pig weights is 0.1 g: 1 kg, and the traditional Chinese medicine compound is used for a long time during the ASFV. At the beginning of this study, 600 sows were selected for experimental verification. The 600 sows were divided into 3 groups: the first group was blank, the second group was a traditional Chinese medicine compound fermented preparation control group, and the third group was a traditional Chinese medicine compound group, which lasted 7 days and was observed and recorded at any time.

TABLE 1

Prevention effect of traditional Chinese medicine compound and fermentation preparation thereof on sows in a pig farm

| Group | Number of testing animals | Mortality | Survival rate | Starting average weight (kg) | End average weight (kg) | Daily weight gain (g) | Death toll (head) |
|---|---|---|---|---|---|---|---|
| Blank group | 200 | 1.5% | 98.5% | 80.8 | 87.5 | 956.67 | 3 |
| Traditional Chinese medicine compound fermented preparation group | 200 | 0.5% | 99.5% | 81.2 | 90.86 | 1380 | 1 |
| Traditional Chinese medicine compound group | 200 | 1% | 99% | 80.6 | 89.28 | 1240 | 2 |

After 7 days of feeding, the daily weight gain of the traditional Chinese medicine compound fermented preparation group is higher than that of the traditional Chinese medicine compound group and the blank group, and the mortality rate of sows is reduced, the survival rate and the daily weight gain of sows are significantly improved.

Embodiment 4 Actual Treatment Effect of the Tetra-Strain Fermentation Product of the Traditional Chinese Medicine Compound on the ASFV A traditional Chinese medicine compound fermented preparation for treating ASFV is provided. The traditional Chinese medicine compound fermented preparation is made from the following raw materials in parts by weight: 20 g of *Codonopsis pilosula*, 20 g of *Atractylodes macrocephala*, 20 g of *Wolfiporia cocos*, 9 g of *Auckiandialappa Lappa* Decne., 15 g of *Terminalia chebula*, 9 g of *Aconitum carmichaeli*, 15 g of *Myristica fragrans*, 15 g of *Cynanchum otophyllum*, 40 g of *Dioscorea polystachya* and 5 g of *Ziziphus jujuba*. The raw materials are mixed and crushed to obtain mixed powder. The mixed powder is placed into a primary fermenter, and the *Bacillus subtilis* and the *Saccharomyces cerevisiae* are inoculated in the primary fermenter to obtain a mixture; the mixture is stirred continuously at 38° C. for 48 h. During stirring, air is introduced into the primary fermenter containing the mixture for aerobic fermentation to obtain an intermediate product. Half of the intermediate product is placed into a secondary fermenter, anaerobic fermentation microorganisms *Lactobacillus acidophilus* and *Bifidobacterium* are added into the secondary fermenter with half of the intermediate product, and the secondary fermenter is placed into a fermentation bag with one-way exhaust valve for anaerobic fermentation at 28° C. for 5 d to obtain a fermented mixture. Contents of the *Bacillus subtilis*, the *Saccharomyces cerevisiae*, the *Bifidobacterium* and the *Lactobacillus acidophilus* are greater than or equal to 1.0× $10^7$ CFU/L. The fermented mixture is directly aseptically filled in a fluid dosage form, and low-temperature spray drying treatment is performed on the fermented mixture to obtain the traditional Chinese medicine preparation fermented with probiotics.

During the peak period of the ASFV from April to June 2021, the traditional Chinese medicine compound fermented preparation was used in a pig farm in Zhumadian, Henan Province, for pigs with symptoms. The traditional Chinese medicine compound fermented preparation was mixed with pig feed to feed the pig based on the weight of freeze-dried traditional Chinese medicine compound fermented preparation once a day. The feeding ratio of the frozen-dried traditional Chinese medicine compound and the pig weights is 0.2 g: 1 kg. During the ASFV, it was fed continuously for 7 days, and after symptom control, it was consolidated for 5 days. In the initial stage of this study, 300 live pigs were selected for the experiment and divided into three groups. The first group was a blank group, the second group was a traditional Chinese medicine compound fermented preparation control group, and the third was a traditional Chinese medicine compound group. Observation and recording were conducted at any time.

TABLE 2

Treatment effect of traditional Chinese medicine compound and fermentation preparation on sows in pig farm

| Group | Number of testing animals | Mortality | Survival rate | Death toll (head) |
|---|---|---|---|---|
| Blank group | 100 | 98 | 2% | 98 |
| Traditional Chinese medicine compound fermented preparation group | 100 | 48 | 52% | 48 |
| Traditional Chinese medicine compound group | 100 | 62 | 38% | 62 |

After 12 days of treatment, the traditional Chinese medicine compound fermented reparation group significantly reduced the mortality rate of live pigs and improved their survival rate.

It should be noted that the above-mentioned implementation schemes should be understood as explanatory and not limiting a scope of protection of the disclosure. The scope of protection of the disclosure shall be subject to claims. For those skilled in the art, some non-essential improvements and adjustments made to the disclosure, without departing from its essence and scope of the disclosure, still fall within the scope of protection of the disclosure.

What is claimed is:

1. A preparation method of a traditional Chinese medicine compound for preventing and treating African swine fever, wherein the traditional Chinese medicine compound is made from the following raw materials in parts by weight:
   10-20 parts of *Codonopsis pilosula*, 10-20 parts of *Atractylodes macrocephala*, 10-20 parts of *Wolfiporia cocos*, 3-9 parts of *Auckiandialappa Lappa* Decne., 5-15 parts of *Terminalia chebula*, 3-9 parts of *Aconitum carmichaeli*, 5-15 parts of *Myristica fragrans*, 9-15 parts of *Cynanchum otophyllum*, 20-40 parts of *Dioscorea polystachya* and 2-5 parts of *Ziziphus jujuba*;

wherein the preparation method comprises:

step 1, weighing, according to the parts by weight, the *Codonopsis pilosula*, the *Atractylodes macrocephala*, the *Wolfiporia cocos*, the *Auckiandialappa Lappa* Decne., the *Terminalia chebula*, the *Aconitum carmichaeli*, the *Myristica fragrans*, the *Cynanchum otophyllum*, the *Dioscorea polystachya* and the *Ziziphus jujuba* to obtain a first mixture, mixing and crushing the first mixture to obtain mixed powder;

step 2, mixing the mixed powder obtained in step 1 with a fermentation medium, placing the fermentation medium mixed with the mixed powder into a primary fermenter, inoculating *Bacillus subtilis* and *Saccharomyces cerevisiae* in the primary fermenter to obtain a second mixture, stirring the second mixture continuously at 30-38 Celsius degrees (° C.) for 12-48 hours (h); wherein air is introduced into the primary fermenter containing the second mixture during the stirring for aerobic fermentation to obtain an intermediate product; and step 3, mixing the intermediate product with the fermentation medium, placing the fermentation medium mixed with the intermediate product into a secondary fermenter, adding anaerobic fermentation microorganisms *Lactobacillus acidophilus* and *Bifidobacterium* into the secondary fermenter to obtain a third mixture, placing the secondary fermenter containing the third mixture into a fermentation bag with a one-way exhaust valve for anaerobic fermentation at 28-42° C. for 1-5 days (d) to obtain a liquid finish product as the traditional Chinese medicine compound; and wherein an inoculation ratio of the *Bacillus subtilis*:the *Saccharomyces cerevisiae*:the *Bifidobacterium*:the *Lactobacillus acidophilus* is 2:1:1:1, and contents of the *Bacillus subtilis*, the *Saccharomyces cerevisiae*, the *Bifidobacterium* and the *Lactobacillus acidophilus* are greater than or equal to $1.0 \times 10^7$ colony forming units per liter (CFU/L).

2. The preparation method as claimed in claim 1, wherein a formula of the fermentation medium in the primary fermenter and the secondary fermenter comprises: 10 grams (g) of refined peptone, 40 g of glucose, 5 g of sodium acetate, 2 g of ammonium citrate, 0.1 g of polysorbate 80, 0.58 g of magnesium sulfate, 0.28 g of manganese sulfate and 1000 milliliters (mL) of distilled water; a power of hydrogen (pH) of the fermentation medium is adjusted to 6-7 by using a 10% sodium hydroxide solution, and then the fermentation medium is autoclaved at 121° C. for 20 minutes (min).

3. The preparation method, as claimed in claim 2, wherein in step 2, an addition ratio of the mixed powder and the fermentation medium is 10-25 g:1 liter (L).

4. The preparation method as claimed in claim 1, wherein a fermentation condition in the primary fermenter and the secondary fermenter is as follows: 0.01-0.2 kilopascals (kPa) of pressure, 15-35 revolutions per minute (r/min) of stirring speed, and 6.1-7.2 of pH value.

\* \* \* \* \*